United States Patent
Singh et al.

(10) Patent No.: US 10,154,826 B2
(45) Date of Patent: Dec. 18, 2018

(54) DEVICE AND METHOD FOR IDENTIFYING ANATOMICAL STRUCTURES

(71) Applicants: Kern Singh, Chicago, IL (US); Sachin Gupta, Hinsdale, IL (US); Michael Oelze, Champaign, IL (US)

(72) Inventors: Kern Singh, Chicago, IL (US); Sachin Gupta, Hinsdale, IL (US); Michael Oelze, Champaign, IL (US)

(73) Assignee: Tissue Differentiation Intelligence, LLC, Chicago, IL (US)

(*) Notice: Subject to any disclaimer, the term of this patent is extended or adjusted under 35 U.S.C. 154(b) by 223 days.

(21) Appl. No.: 14/329,940

(22) Filed: Jul. 12, 2014

(65) Prior Publication Data

US 2016/0354056 A1    Dec. 8, 2016

Related U.S. Application Data

(60) Provisional application No. 61/847,517, filed on Jul. 17, 2013, provisional application No. 61/867,534, (Continued)

(51) Int. Cl.
*A61B 8/08* (2006.01)
*A61B 8/12* (2006.01)
(Continued)

(52) U.S. Cl.
CPC ............ *A61B 8/085* (2013.01); *A61B 8/12* (2013.01); *A61B 8/4455* (2013.01); *A61B 8/5223* (2013.01); *A61B 17/0206* (2013.01); *A61B 42/10* (2016.02); *A61B 2017/00438* (2013.01); *A61B 2017/0262* (2013.01);
(Continued)

(58) Field of Classification Search
None
See application file for complete search history.

(56) References Cited

U.S. PATENT DOCUMENTS 5,224,480 A  7/1993 Yamada et al.
5,361,767 A  11/1994 Yukov
(Continued)

FOREIGN PATENT DOCUMENTS

CN  102940510 A  2/2013
CN  105030279 A  11/2015
(Continued)

OTHER PUBLICATIONS

Olafsson et al., "Ultrasound Current Source Density Imaging of a Time-varying Current Field in a Multielectrode Nerve Chamber". International Ultrasound Symposium, Vancouver, BC, Canada, 2006, pp. 5-8.*
Suk et al., "Ultrasound of Peripheral Nerves". Curr. Neurol. Neurosci. Rep. Feb. 2013; 13(2), pp. 1-16.*
Ihnatsenka et al., "Ultrasound: basic understanding and learning the language". Int. J Shoulder Surg. 2010; 4(3): 55-62.*
(Continued)

*Primary Examiner* — Katherine Fernandez
*Assistant Examiner* — Yi-Shan Yang
(74) *Attorney, Agent, or Firm* — Banner & Witcoff, Ltd.

(57) ABSTRACT

A method for identifying a target anatomy by use of a device having an ultrasound transducer. Using the ultrasound transducer, a portion of a patient's anatomy is scanned during a scanning process. A voltage trace of the patient's anatomy is determined and compared to a predetermined trace. If the voltage trace of the patient's anatomy matches the predetermined trace, a notification may be output.

20 Claims, 18 Drawing Sheets

Related U.S. Application Data filed on Aug. 19, 2013, provisional application No. 61/868,508, filed on Aug. 21, 2013, provisional application No. 61/899,179, filed on Nov. 2, 2013, provisional application No. 61/921,491, filed on Dec. 29, 2013, provisional application No. 61/929,083, filed on Jan. 19, 2014, provisional application No. 61/977,594, filed on Apr. 9, 2014.

(51) Int. Cl.

| | | |
|---|---|---|
| *A61B 8/00* | (2006.01) | |
| *A61B 17/02* | (2006.01) | |
| *A61B 42/10* | (2016.01) | |
| *A61B 17/34* | (2006.01) | |
| *A61B 34/20* | (2016.01) | |
| *A61B 17/00* | (2006.01) | |
| *A61B 90/00* | (2016.01) | |

(52) U.S. Cl.
CPC .............. *A61B 2017/3413* (2013.01); *A61B 2034/2063* (2016.02); *A61B 2090/373* (2016.02); *A61B 2090/378* (2016.02); *A61B 2090/3735* (2016.02); *A61B 2090/3966* (2016.02)

(56) References Cited

U.S. PATENT DOCUMENTS

| | | |
|---|---|---|
| 5,935,074 A | 8/1999 | Mo et al. |
| 6,048,311 A | 4/2000 | Washburn et al. |
| 6,120,445 A | 9/2000 | Grunwald |
| 6,126,601 A | 10/2000 | Gilling |
| 6,135,961 A | 10/2000 | Pflugrath et al. |
| 6,181,810 B1 | 1/2001 | Zhang et al. |
| 6,248,072 B1 | 6/2001 | Murkin |
| 6,248,073 B1 | 6/2001 | Gilbert et al. |
| 6,251,073 B1 | 6/2001 | Imran et al. |
| 6,287,259 B1 | 9/2001 | Grunwald |
| 6,325,759 B1 | 12/2001 | Pelissier |
| 6,358,206 B1 | 3/2002 | Cohen-Bacrie |
| 6,379,304 B1 | 4/2002 | Gilbert et al. |
| 6,383,139 B1 | 5/2002 | Hwang et al. |
| 6,413,217 B1 | 7/2002 | Mo |
| 6,416,475 B1 | 7/2002 | Hwang et al. |
| 6,450,959 B1 | 9/2002 | Mo et al. |
| 6,475,149 B1 | 11/2002 | Sumanaweera |
| 6,491,636 B2 | 12/2002 | Chenal et al. |
| 6,514,202 B2 | 2/2003 | Grunwald |
| 6,530,888 B2 | 3/2003 | Smith et al. |
| 6,537,217 B1 | 3/2003 | Bjærum et al. |
| 6,544,181 B1 | 4/2003 | Buck et al. |
| 6,569,101 B2 | 5/2003 | Quistgaard et al. |
| 6,572,547 B2 | 6/2003 | Miller et al. |
| 6,579,239 B1 | 6/2003 | Avinash et al. |
| 6,579,244 B2 | 6/2003 | Goodwin |
| 6,679,843 B2 | 1/2004 | Ma et al. |
| 6,741,895 B1 | 5/2004 | Gafni et al. |
| 6,746,402 B2 | 6/2004 | Ustuner |
| 6,849,047 B2 | 2/2005 | Goodwin |
| 6,875,176 B2 | 4/2005 | Mourad et al. |
| 6,896,658 B2 | 5/2005 | Ji et al. |
| 6,945,938 B2 | 9/2005 | Grunwald |
| 7,074,188 B2 | 7/2006 | Nair et al. |
| 7,141,020 B2 | 11/2006 | Poland et al. |
| 7,175,597 B2 | 2/2007 | Vince et al. |
| 7,215,802 B2 | 5/2007 | Klingensmith et al. |
| 7,347,821 B2 | 3/2008 | Skyba et al. |
| 7,463,759 B2 | 12/2008 | Klingensmith et al. |
| 7,466,256 B2 | 12/2008 | Brueske et al. |
| 7,472,597 B2 | 1/2009 | Zhang et al. |
| 7,481,769 B2 | 1/2009 | Karasawa |
| 7,680,307 B2 | 3/2010 | Sathyanarayana |
| 7,682,309 B2 | 3/2010 | Ji et al. |
| 7,686,766 B2 | 3/2010 | Quistgaard et al. |
| 7,729,533 B2 | 6/2010 | Sathyanarayana |
| 7,804,990 B2 | 9/2010 | Kiraly et al. |
| 7,815,572 B2 | 10/2010 | Loupas |
| 7,823,453 B2 | 11/2010 | Zhang et al. |
| 7,876,934 B2 | 1/2011 | Georgescu et al. |
| 7,920,922 B2 | 4/2011 | Gharib et al. |
| 8,010,181 B2 | 8/2011 | Smith et al. |
| 8,041,413 B2 | 10/2011 | Barbagli et al. |
| 8,105,237 B2 | 1/2012 | Waters et al. |
| 8,105,239 B2 | 1/2012 | Specht |
| 8,219,177 B2 | 7/2012 | Smith et al. |
| 8,219,178 B2 | 7/2012 | Smith et al. |
| 8,265,355 B2 | 9/2012 | Zhao et al. |
| 8,568,317 B1 | 10/2013 | Gharib et al. |
| 8,663,116 B2 | 3/2014 | Hamilton, Jr. |
| 8,679,018 B2 | 3/2014 | McLaughlin et al. |
| 8,715,187 B2 | 5/2014 | Landberg Davis et al. |
| 8,715,292 B2 | 5/2014 | Glazer |
| 8,754,888 B2 | 6/2014 | Virtue et al. |
| 8,870,773 B2 | 10/2014 | Narouze |
| 8,876,721 B2 | 11/2014 | Nakamura |
| 9,058,649 B2 | 6/2015 | Harrison et al. |
| 9,086,474 B2 | 7/2015 | Li et al. |
| 9,125,589 B2 | 9/2015 | Somes |
| 9,251,593 B2 | 2/2016 | Villain et al. |
| 9,277,902 B2 | 3/2016 | Mullick et al. |
| 9,324,155 B2 | 4/2016 | Mendonca et al. |
| 9,592,027 B2 | 3/2017 | Nair |
| 9,597,054 B2 | 3/2017 | Kudavelly et al. |
| 9,655,592 B2 | 5/2017 | Schroecker et al. |
| 2003/0045797 A1 | 3/2003 | Christopher et al. |
| 2003/0125629 A1 | 7/2003 | Ustuner |
| 2005/0101866 A1 | 5/2005 | Goodwin |
| 2005/0245822 A1* | 11/2005 | Dala-Krishna ........ A61B 8/065 600/433 |
| 2007/0078342 A1 | 4/2007 | Jago |
| 2007/0167802 A1 | 7/2007 | Rigby et al. |
| 2007/0238953 A1 | 10/2007 | Lucassen et al. |
| 2008/0009738 A1 | 1/2008 | Li et al. |
| 2008/0015439 A1 | 1/2008 | Raju et al. |
| 2008/0077010 A1 | 3/2008 | Cohen-Solal et al. |
| 2008/0119727 A1* | 5/2008 | Barbagli .................. A61B 5/06 600/424 |
| 2008/0183076 A1* | 7/2008 | Witte .................. A61B 5/0093 600/438 |
| 2008/0188749 A1 | 8/2008 | Rasche et al. |
| 2009/0131791 A1 | 5/2009 | Clark |
| 2009/0171205 A1 | 7/2009 | Kharin et al. |
| 2010/0010367 A1 | 1/2010 | Foley et al. |
| 2010/0204567 A1 | 8/2010 | Narouze |
| 2010/0286518 A1 | 11/2010 | Lee et al. |
| 2010/0286519 A1 | 11/2010 | Lee et al. |
| 2011/0098531 A1* | 4/2011 | To ..................... A61B 17/1671 600/114 |
| 2011/0213250 A1 | 9/2011 | Vion et al. |
| 2011/0263985 A1 | 10/2011 | Gauthier et al. |
| 2011/0319765 A1 | 12/2011 | Gertner et al. |
| 2012/0116218 A1 | 5/2012 | Martin et al. |
| 2012/0152021 A1 | 6/2012 | Ma et al. |
| 2012/0184853 A1 | 7/2012 | Waters |
| 2012/0197124 A1 | 8/2012 | Nakamura |
| 2012/0310064 A1 | 12/2012 | McGee |
| 2012/0310087 A1 | 12/2012 | Miyaki et al. |
| 2013/0023767 A1 | 1/2013 | Mammone |
| 2013/0085394 A1 | 4/2013 | Corbett, III et al. |
| 2013/0090554 A1 | 4/2013 | Zvuloni et al. |
| 2013/0172742 A1 | 7/2013 | Rankin et al. |
| 2014/0005530 A1 | 1/2014 | Liu et al. |
| 2014/0018668 A1* | 1/2014 | Zheng .................. A61B 8/4254 600/424 |
| 2014/0155748 A1 | 6/2014 | Pernisa et al. |
| 2014/0163375 A1 | 6/2014 | Wasielewski |
| 2014/0213905 A1 | 7/2014 | Saad et al. |
| 2014/0221838 A1 | 8/2014 | Loupas et al. |
| 2016/0007858 A1 | 1/2016 | Hendriks et al. |
| 2016/0098621 A1 | 4/2016 | Tahmasebi Maraghoosh et al. |
| 2016/0174934 A1 | 6/2016 | Cong et al. |
| 2016/0238568 A1 | 8/2016 | Feleppa et al. |

(56) References Cited

U.S. PATENT DOCUMENTS

| 2016/0317035 A1 | 11/2016 | Hendriks et al. |
| 2016/0317119 A1 | 11/2016 | Tahmasebi Maraghoosh et al. |
| 2016/0324584 A1 | 11/2016 | Tahmasebi Maraghoosh et al. |
| 2016/0338673 A1 | 11/2016 | Imai |
| 2016/0350620 A1 | 12/2016 | Rao et al. |
| 2017/0007161 A1 | 1/2017 | Zou et al. |
| 2017/0112473 A1 | 4/2017 | Samset |
| 2017/0119356 A1 | 5/2017 | Steininger et al. |
| 2017/0238907 A1 | 8/2017 | Kommu CHS |
| 2017/0296061 A1 | 10/2017 | Murakoshi et al. |

FOREIGN PATENT DOCUMENTS

| CN | 106491161 A | 3/2017 |
| DE | 102004040869 B3 | 12/2005 |
| JP | H05337111 A | 12/1993 |
| JP | H11169375 A | 6/1999 |
| JP | 2006223512 A | 8/2006 |
| JP | 2008520317 A | 6/2008 |
| WO | 2006072050 A2 | 7/2006 |
| WO | 2014186899 A1 | 11/2014 |
| WO | 2016205936 A1 | 12/2016 |

OTHER PUBLICATIONS

Tufail et al., "Transcranial pulsed ultrasound stimulates intact brain circuits". Neuron 2010, 66, 681-694.*
Sep. 1, 2016—International Search Report and Written Opinion—PCT/US2016/026206.
Lango, et al., "Navigation Laparoscopic Ultrasound in Abdominal Soft Tissue Surgery: Technical Overview and Perspectives", Int J CARS (2012) pp. 7:585-7:599.
Light, et al., "Real-Time 3D Laparoscopic Ultrasonography", Ultrasonic Imaging 27, pp. 129-144 (2005).
Hozumi, et al., "Easy and Accurate Targeting of Deep-Seated Hepatic Tumors Under Laparoscopy with a Forward-Viewing Convex-Arrar Transducer", Surg Endosc (2003) 17, Springer-Verlag New York Inc. 2003, pp. 1256-1260.
Sep. 1, 2016—(PCT) International Search Report PCT/US16/26206.
Jan. 20, 2016—(PCT) International Search Report PCT/US2015/050404.
May 11, 2017—(WO) International Search Report and Written Opinion Appn PCT/US2017/21192.
Feb. 27, 2018—(JP) Office Action Appn 2017-534894.
Jun. 6, 2018—(EP) Extended European Search Report.

* cited by examiner

DEVICE AND METHOD FOR IDENTIFYING ANATOMICAL STRUCTURES

PRIORITY CLAIM

This application claims priority to U.S. Provisional Patent Application Ser. No. 61/847,517, filed Jul. 17, 2013, entitled Direct Visualization Dissector and Retractor System for Minimally Invasive Procedures, No. 61/867,534, filed Aug. 19, 2013, entitled Ultrasonic Visualization, Dissection, and Retraction System for Minimally Invasive Procedures, No. 61/868,508, filed Aug. 21, 2013, entitled OCT Visualization, Dissection, and Retraction System for Minimally Invasive Procedures, No. 61/899,179, filed Nov. 2, 2013, entitled Nerve Detection System, No. 61/921,491, filed Dec. 29, 2013, entitled System and Method for Identifying Anatomical Structures Ultrasonically, No. 61/929,083, filed Jan. 19, 2014, entitled System and Method for Identifying Anatomical Structures Ultrasonically, and No. 61/977,594, filed Apr. 9, 2014, entitled System and Method for Identifying Anatomical Structures Ultrasonically Employing Two or More Transduces, each of which is hereby incorporated by reference.

BACKGROUND

Surgical techniques utilizing minimally invasive surgery (or "MIS") are being rapidly adapted to replace current traditional "open" surgical procedures. "Open" procedures typically require larger skin incisions that may cause significant collateral damage to uninvolved anatomic structures. To allow for direct surgical visualization, intervening soft tissue is cut and potentially excised (tendons, ligaments, facet capsules and muscle).

To the contrary, minimally invasive techniques, which may also be referred to as "percutaneous," involve significantly smaller incisions and are less traumatic to the patient anatomy. Soft tissues are preserved with minimal collateral damage to the uninvolved anatomy. Typical benefits of MIS may include decreased blood loss, decreased postoperative pain, smaller scar formation, decreased cost, and a faster rehabilitation for the patient, as compared to "open" or conventional surgical techniques.

Minimally invasive surgery techniques are currently being adapted to a variety of surgical procedures. For example, minimally invasive techniques in the form of laparoscopic procedures, such as a laparoscopic colectomy for carcinoma of the colon, have been developed. More recently, surgeons have utilized MIS in the setting of spinal surgery. Current MIS techniques, however, are unable to accurately and consistently detect and avoid key anatomical features, such as neural elements potentially resulting in profound neurological sequelae.

BRIEF SUMMARY

In one embodiment of the present invention, a device is provided for minimally invasive surgery having a proximal portion. a distal portion, a main body formed between the proximal and distal portions of the device having a longitudinal axis and at least two ultrasound transducers disposed at the distal portion of the main body, where at least one of the transducers is angled with respect to the longitudinal axis of the main body where the at least one transducer is configured to scan a region that extends at least partially radially away from the longitudinal axis of the main body.

In another embodiment, a device for minimally invasive surgery includes a proximal portion, a distal portion, a main body formed between the proximal and distal portions of the device having a longitudinal axis and at least one ultrasound transducer disposed within the distal portion of the device and configured to scan a region adjacent to a distal end of the distal portion of the device.

In another embodiment, a method for identifying a target anatomy is provided with a device having a distal portion and at least one ultrasound transducer at least partially disposed within a main body of the device, where the method includes scanning a patient's anatomy for the target anatomy, determining a voltage trace of the patient's anatomy, comparing the voltage trace of the patient's anatomy to a predetermined voltage trace of the target anatomy, and sending a notification if the voltage trace of the patient's anatomy matches the predetermined voltage trace of the target anatomy.

DETAILED DESCRIPTION

Figure 1:
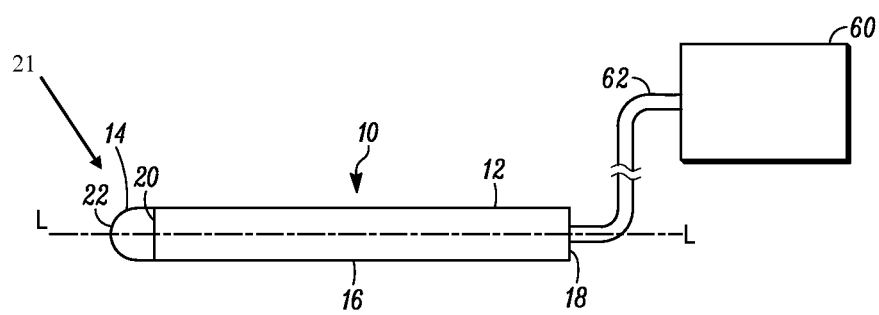
FIG. 1 is a side view of one embodiment of a device.

To help understand this invention, the following definitions are provided with reference to terms used in this application.

Throughout this specification and in the appended claims, when discussing the application of this invention with respect to the body's tissue, spine or other neural elements, the term "proximal" with respect to such a device is intended to refer to a location that is, or a portion of the device that is, closer to the user. The term "distal" is intended to refer to a location that is, or a portion of the device, further away from the user.

The embodiments below are described with reference to the drawings in which like elements are referred to by like numerals. The relationship and functioning of the various elements are better understood by the following detailed description. The embodiments as described below are by way of example only and the invention is not limited to the embodiments illustrated in the drawings.

This invention relates to a device that is capable of detecting target anatomical structures using ultrasound and/or Optical Coherence Tomography technology as the device is being advanced through a patient's anatomy. The device may have a distal portion having a tip, where the tip can be used to dissect a patient's anatomy without puncturing or tearing the patient's anatomy and while simultaneously allowing the device to inspect the anatomy as it is being dissected by the tip. While the device discussed herein is discussed in the context of a device that can be held by a user, it is contemplated that the device and/or parts of the device may be used during automated procedures such as those being performed by da Vinci® robotic and other similar systems.

In one embodiment, shown in FIG. 1, the device 10 has a proximal portion 12 and a distal portion 14 with a main body 16 disposed between the proximal and distal portions 12, 14. The main body 16 has a proximal end 18 and a distal end 20 and is defined by a longitudinal axis L. The proximal end 18 may have a handle (not shown) or gripping portion (not shown) attached thereto. The length of the main body 16 may vary, but can include a length of 50 to 300 mm but may also fall outside of this range. Similarly, the outer diameter of the main body 16 may vary and can include an outer diameter of between 3 mm and 20 mm. The main body 16 can be made out of any preferable surgical grade material, including but not limited to, medical grade polymer including PEEK (polyether ether ketone), stainless steel, carbon fiber, and titanium. The main body 16, and all of the components of the device 10 generally, may contain radio-opaque markers to allow a user to detect the location of the device 10 with respect to the anatomy of a patient via radiographic imaging.

As shown in FIG. 1, the distal portion 14 of the device 10 includes a tip 22. The tip 22 in this embodiment is hemispherical in shape, but it is contemplated that the tip 22 may also be of a different shape. For example, and without limitation, the tip 22 have a semi-spherical, conical, pyramidal, spear or aspherical shape. The tip 22 is configured to dissect a patient's anatomy, such as a muscle, without tearing or disrupting the patient's anatomy as it passes through the tissue. As a result, the outer diameter of the tip 22 has a diameter that can range anywhere between 1 mm and 50 mm and preferably between 2 mm and 9 mm. It is appreciated that the outer diameter of the tip 22 may fall outside of this range as well. It is appreciated that the tip 22 is optional such that particular embodiments of the device 10 may not include the tip 22.

Figure 2:
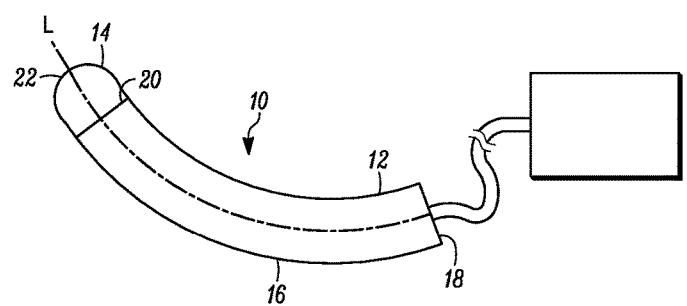
FIG. 2 is a side view of another embodiment of the device of FIG. 1.

In the embodiment shown in FIG. 1, the main body 16 of the device 10 is substantially straight. However, it is contemplated that the main body 16 may have different shapes, including having a curved shape with a non-zero radius of curvature. One example of such an embodiment is should in FIG. 2, which can be used for minimally invasive surgery requiring access through the presacral space of a patient. The main body 16 may also take on an "L", "C", "U" shape or a shape therebetween.

The device 10 may include ultrasonic capability and one purpose of this device is to serve as an instrument that features a specifically patterned array of high frequency ultrasound transducers and a monitoring system that collects spectral properties of specific tissue in the body. For example, the system may be able to detect the spectral properties of muscle, fat, nerve and bone. As the anatomy is stimulated by the ultrasound transducer(s), it will emit a specific spectral property that can be detected by the monitoring system. The system will examine scan line images and seek to specific parameters of amplitude and other spectral content in order to differentiate the signals coming from the nerve and signals coming from surrounding tissues. For example, we have determined that nerve tissue is hypoechoic with the surrounding tissue. However there are internal structures that provide features in the signal that identify the nerve from single scan lines. The system will inform the user that the device is adjacent to or proximate to the specific type of anatomy that is detected by the system. The device can allow a surgeon to identify and avoid certain portions of a patient's anatomy (e.g. nerve) when performing a minimally invasive procedure.

Figure 3:
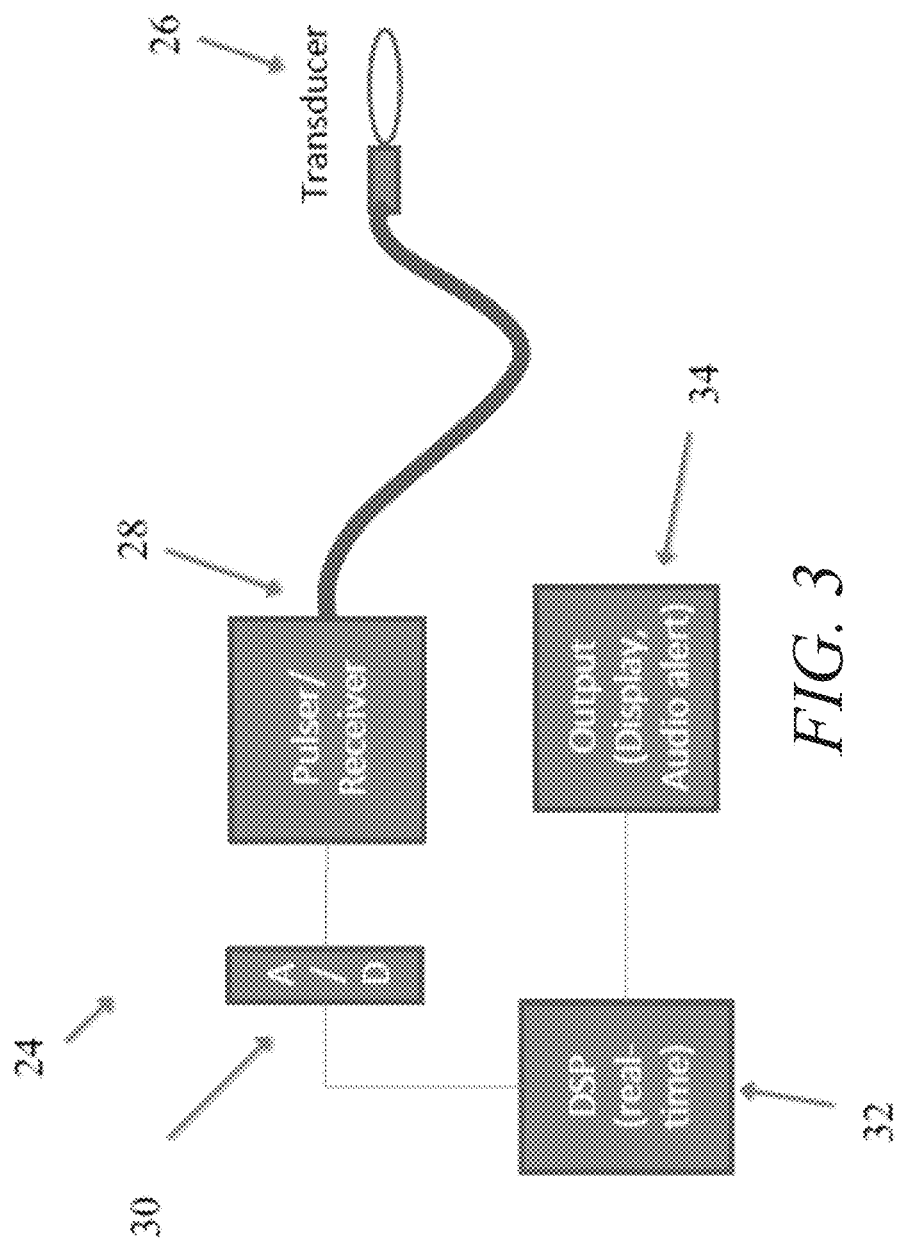
FIG. 3 is a functional diagram of the ultrasound imaging system that may be used in one embodiment of the present invention.
Figure 4:
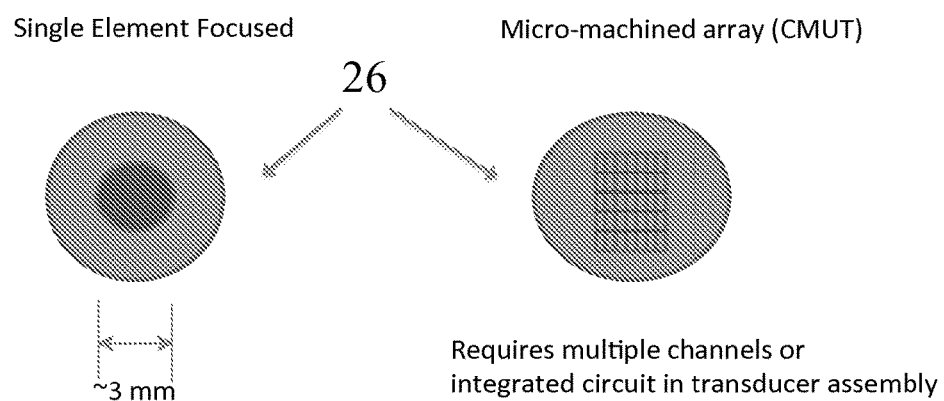
FIG. 4 is a diagram of an ultrasound transducer that may be used in one embodiment of the present invention.
Figure 5:
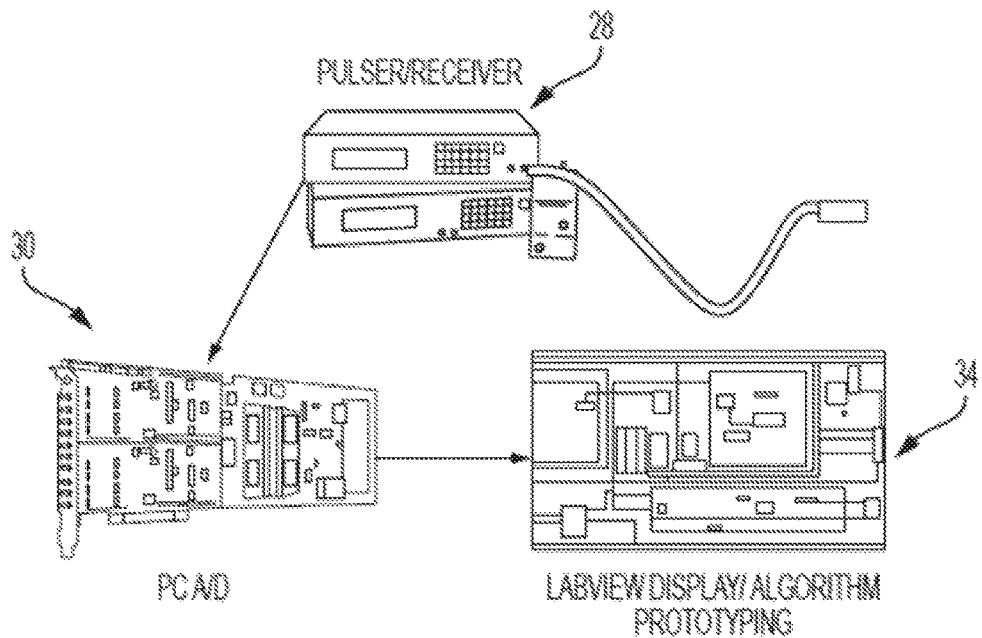
FIG. 5 is another functional diagram of one embodiment of the ultrasound imaging system that may be used in an embodiment of the present invention.

The device 10 may be equipped with ultrasound imager 24 to detect a patient's anatomy as shown in FIGS. 3-5. The ultrasound imager 24 may include a transducer 26 that is configured to emit sound waves may be disposed at the distal end 20 of the device 10. As shown in FIG. 4, the transducer 26 can be either a single element focused transducer, which can have a frequency operation range that includes an operating range of approximately 10-40 MHz, but can be higher or lower than this range of frequencies, or alternatively a micro machined array (CMUT) having multiple channels. The desirable frequency may vary depending on the application and target anatomy. For example, in one embodiment the selected frequency or range of frequencies will be ideal for detecting nerve from surrounding tissues and adjacent anatomy on b-mode images based on image texture and echogenicity. Reliably distinguishing between nerve and muscle tissue in real time will require quantitative approaches, which require calibrating the system to estimate tissue-specific properties. A meta-analysis comparing ultrasound to nerve-stimulation showed superior outcomes for ultrasound guidance.

As shown in FIGS. 3 and 5, the transducer 26 may be in communication with a RF-pulser/receiver 28, which may be in communication with an analog to digital converter 30, which may then be in communication with a digital signal processor 32 and then an output 34 such as a monitor.

In one embodiment, the transducer 26 converts an electric signal or pulse generated from the RF-pulser/receiver 28 into a sound wave and then converts a reflected sound wave back into an electrical signal. The ultrasound transducer 26 launches short, high-frequency non-damaging sound pulses into the tissue, and then waits to hear the reflection from the tissue. Since the speed of sound in tissues is high (~1500 m/s), this process takes only a few milliseconds to image a few millimeters of tissue. As referenced above, the RF-pulser/receiver 28 generates an electrical impulse that may be sent via a cable to the transducer 26 to generate a sound wave, and also receives a signal from the transducer 26 generated by the reflected sound waves that the transducer receives 26. The analog to digital converter 30 converts the analog, radiofrequency signal received from the transducer 26 into a digital form that a computer can analyze. The digital signal processer 32 processes the digitized signal received from the digital converter 30. Signal filtering and processing operations are programmed into the software to detect the reflected signal properties of the tissue, and distinguish between nerve and muscle tissues in real-time. Once a nerve tissue signature is detected, a software system may communicate with the output display 34. The output 34 may include a visual monitor that displays the anatomy (e.g. via actual images or programmable color configurations (red/yellow/green)) or an audible indicator (e.g. alarm or a "beep") when the device 10 encounters/detects the presence of target anatomy (e.g. nerve) within a predetermined range (e.g. 1 mm to 10 cm), or a combination of both.

It is appreciated that one or more of these components may be in wireless communication with one another, may be combined into one or components, and other additional components may be in communication between each of these components or one or more identified components may not be included in a particular embodiment.

In one embodiment, the outer diameter of the transducer 26 may be approximately 3 mm, but can range anywhere between approximately 1 mm and 10 mm. Further, the transducer 26 is configured to be disposed in a variety of locations with respect to the device 10. The transducer 26 may be disposed at the distal end 20 of the main body 16 or at the tip 22 portion of the distal end 20. The transducer 26 may also be removable such that it can be removably disposed within a conduit 36 formed within the device 10 and removed once a working space 38 is identified and accessible. The working space 38 is the space created by the device 10 within the patient's anatomy.

It can be appreciated that the transducers 26 may be side positioned (e.g. on either side of the main body 16) so as to provide for multi-directional scanning of the patient's anatomy to detect the nerve. The side positioned transducers are configured to scan the anatomy around in a circumferential direction around the main body 16 to detect the nerve (or other target anatomy) that was not detected by the transducer positioned at the distal end 20 of the main body 16. The multi-directional scanning enables the system to generate a scan image of the patient's anatomy in multiple directions as the device 10 is advanced through the patient's anatomy.

Figure 6:
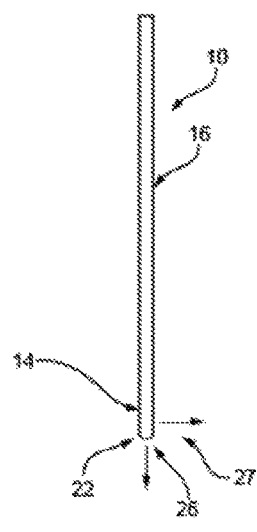
FIG. 6 is one embodiment of the device having more than one ultrasound transducer disposed therein.

For example, as shown in FIG. 6, the device 10 may include at least one ultrasound transducer 26 (such as a high frequency ultrasound transducer) that is used to stimulate a patient's anatomy, such as muscle, fat, nerve, and bone. A series of transducers 26 can be disposed along the length of the device 10 to allow for a wider pattern of ultrasonic stimulation of the surrounding anatomy. In this embodiment, there is one transducer 26 on the distal end of the device 10 that emits an ultrasonic frequency in a direction that is substantially parallel to the longitudinal axis of the device 10. There is another transducer 26 that is adjacent to the first transducer 27 that emits ultrasonic frequency along a path that is substantially perpendicular to the longitudinal axis of the device 10. It can be appreciated that the transducers 26 can be orientated in any direction that is required for the particular application.

Figure 7:
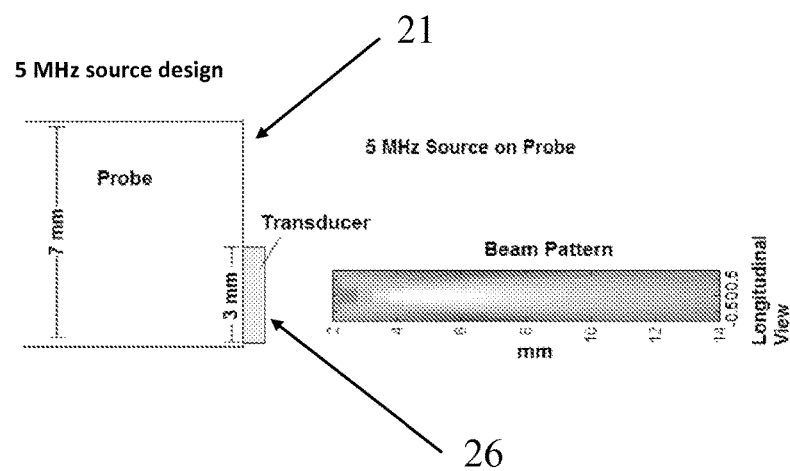
FIG. 7 is another embodiment of the device having one ultrasound transducer disposed therein.
Figure 8:
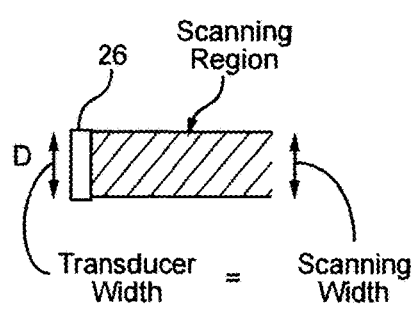
FIG. 8 depicts the scanning width of a transducer.

FIG. 7 depicts one embodiment where a 5 MHz transducer 26 is place on the distal end 21 of the device. In this embodiment, the diameter of the transducer 26 is 3 mm and is forward facing. In this embodiment, the scanning range is approximately 14 mm It is understood that the area of the scanning region (hatched section in FIG. 8) by a transducer 26 may not exceed the outer diameter of the transducer. This is because the scanning width is typically circumscribed by the outer diameter of the transducer 26 and the peripheral limitations of the transducer 26 such that the transducer 26 cannot identify or scan a region that lies beyond of the diameter of transducer 26, as shown in FIG. 8.

Figure 9:
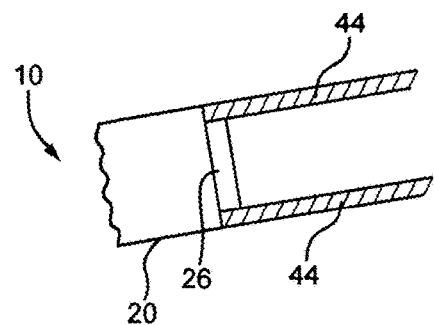
FIG. 9 depicts the scanning width of a transducer in one configuration.

It follows that when the transducer 26 is housed within a device 10, such at those disclosed herein, the transducer 26 is typically unable to scan the region that is in directly front of (distal to) the outer portions of the device that house the transducer 26. This region 44 is depicted in FIG. 9. This means that the target anatomy will go undetected if it is positioned beyond the scanning region of the transducer 26. This may not be an issue for some applications.

Figure 11:
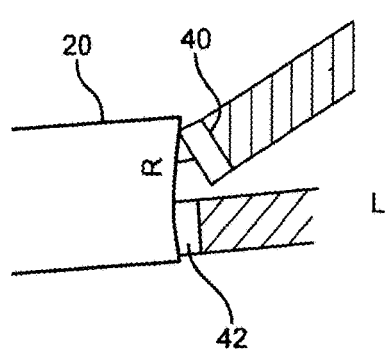
FIG. 11 depicts the scanning width of the embodiment of FIG. 10.
Figure 10:
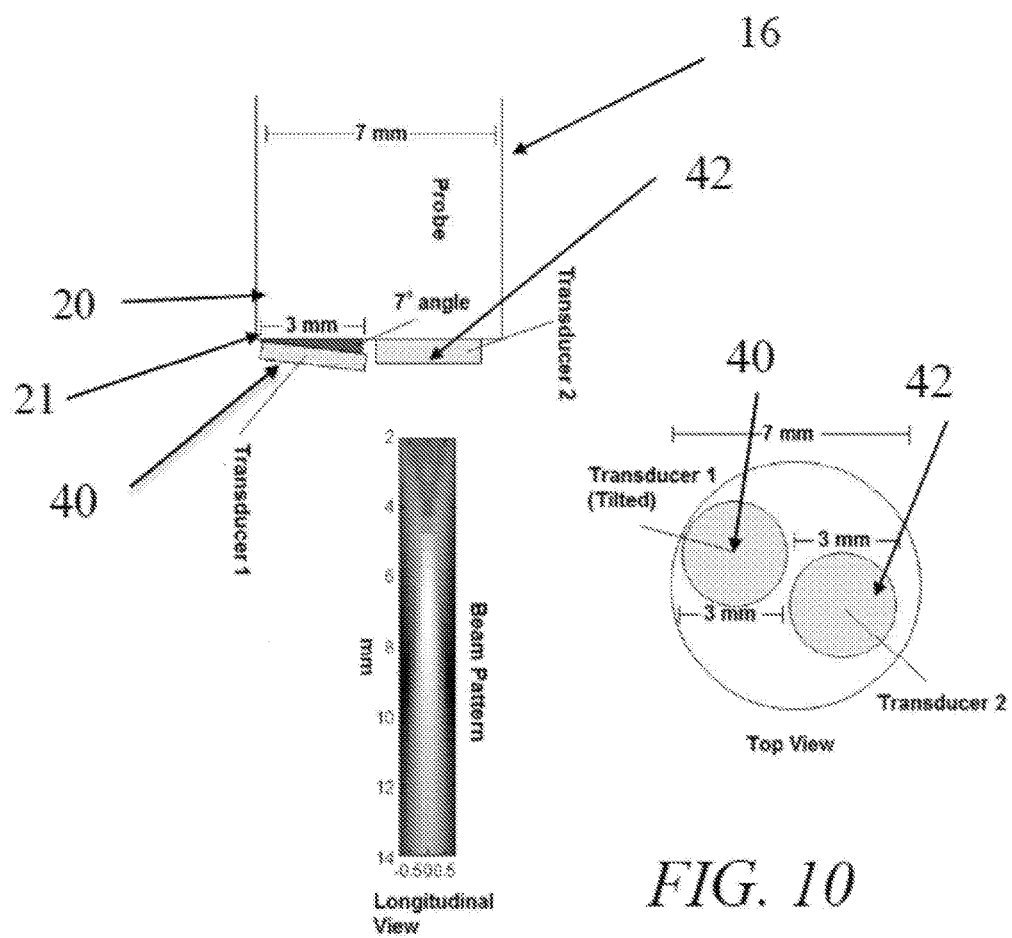
FIG. 10 is another embodiment of the present invention where one of the transducers is positioned at an angle with respect to the other transducer.

If it is desirable to detect target anatomy that is just beyond the scanning region of the transducer 26 (i.e. outside of the scanning diameter), however, the device 10 may include two or more transducers positioned at an angle relative to one another. For example, as shown in FIGS. 10 and 11, the first transducer 40 is positioned at an angle with respect to the outer edge of the main body 16. The angle may be measured from the face of distal end 21 of the device 10, or may be measured from the horizontal axis that intersects the longitudinal axis of the device 10. The angle $\alpha$ in this embodiment is 7° but it is appreciated that it can vary from 0° to 180° depending on the particular embodiment. Further, in this embodiment, it is shown that the angle is formed between the edge of the transducer 26 that is adjacent to the outer edge of the main body 16.

Figure 12:
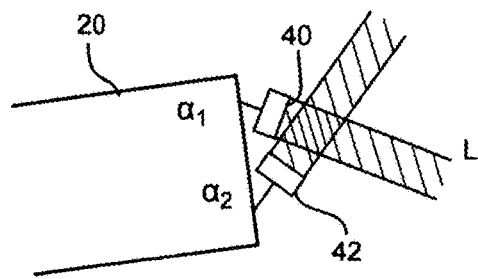
FIG. 12 is yet another embodiment of the present invention where two transducers are angled towards the longitudinal axis of the device.

It is appreciated that the transducer 40 may be angled with respect to any portion of the main body 16. For example, the first transducer 40 may be angled by pivoting the first transducer 40 about the portion that is positioned along, or closest to, the longitudinal axis of the main body 16 as shown in FIG. 12. Specifically, as shown in FIG. 12, the transducers 40, 42 are angled towards the longitudinal axis of the main body 16 such that the angle of tilt, $\alpha_1$ $\alpha_2$, are measured as the angle of the transducer from the longitudinal axis of the main body 20.

In the embodiment shown in FIG. 10, the first transducer 40 is positioned at such an angle (i.e. 7° from the edge of the main body 16) to allow it to scan a region that extends beyond the outer edge of the main body 16. Angling the first transducer 40 allows the device 10 to scan and detect any target anatomy that resides outside of the scanning region of a transducer that is not angled with respect to the main body 16 of the device. The region that can be scanned by the first angled transducer 40 in this particular embodiment is shown in FIG. 10.

In the embodiment shown in FIG. 10, the two transducer elements that fit on the tip of a device 10 with the goal of detecting backscattered signals at a standoff of up to 1 cm from the probe tip 22 to detect the presence of nerve bundles in the pathway of the probe. This embodiment provides a probe with 5 and 10 MHz transducers of element with 3 mm. The fields (beam patterns) from the sources were modeled using field II assuming an element diameter of 3 mm and a focal number of 3 (f/3).

In this design (10 MHz), the two transducer elements 40, 42 are on top of the probe. The tiled element 40 faces outward with an angle of tilt of 7°. The tiled element has one end at the edge of the probe. The un-tilted element 42 is centered at around 2 mm from the edge of the distal portion of the device 10. This configuration allows the device 10 to be rotated as it is snaked through the tissue so that the cross sectional surface area of the probe is at least 1 cm above the probe surface.

The diameter of the transducers 40, 42 may vary and can range from 1 mm to 20 mm. For example, in the embodiment shown in FIG. 10, the first transducer and second transducers 40, 42 each have a diameter of approximately 3 mm. It is not necessary for the transducers to have the same diameter of one another and can be staggered as shown in the top view of FIG. 10.

The main body 16 can be rotated so as to allow the first transducer 40 to scan the entire outer region to detect whether any target anatomy is present that is just beyond the scanning area of a forward facing transducer. By rotating the main body 16 about its longitudinal axis, the first transducer 40 can scan the outer region that does not fall within the scanning region of a transducer that is not angled with respect to the main body 16 of the device.

It can be appreciated that the number of angled transducers may vary and can be positioned at various angles with respect to the distal end of the main body 16. For example, as shown in FIG. 12, the first and second transducers 40, 42 are positioned toward one another so that their scanning areas cross to provide a scan of the area distal to the distal portion 20 of the device 10 and a region beyond the area directly in front of to the outer diameter of the transducers 40, 42 as shown in FIG. 9. Also, the transducers 40, 42 may be positioned at an angle on more than one axis with respect to the distal end of the main body 16.

The device 10 can be configured to determine the b-mode scans of the patient's anatomy and associated data, e.g. the voltage trace from a scan line in the b-mode image. It can be appreciated that the voltage trace for certain anatomical parts (e.g. nerve) has a unique voltage trace that can be used to detect like anatomical parts within the patient's anatomy. One way to detect like anatomical parts is by comparing the voltage trace from a scan line of a b-mode image to the known voltage trace from the scan line of the target anatomy.

Specifically, the b-mode scans (and associated data, e.g. a-scan lines and voltage traces) captured by the device 10 are compared to the pre-determined b-mode scans (and associated data) of known anatomical features (e.g. nerve) to determine whether the region captured by the b-mode scan from the device 10 contain the target anatomy. The discussion below is directed to the experiment used to determine the target ultrasonic frequency that can be used to detect nerve using the device 10 and whether the b-mode scan images captured by the device 10, which is inserted into the patient's anatomy, is comparable to results captured by traditional non-invasive ultrasound devices. Both target objectives were accomplished using the following process.

Figure 13:
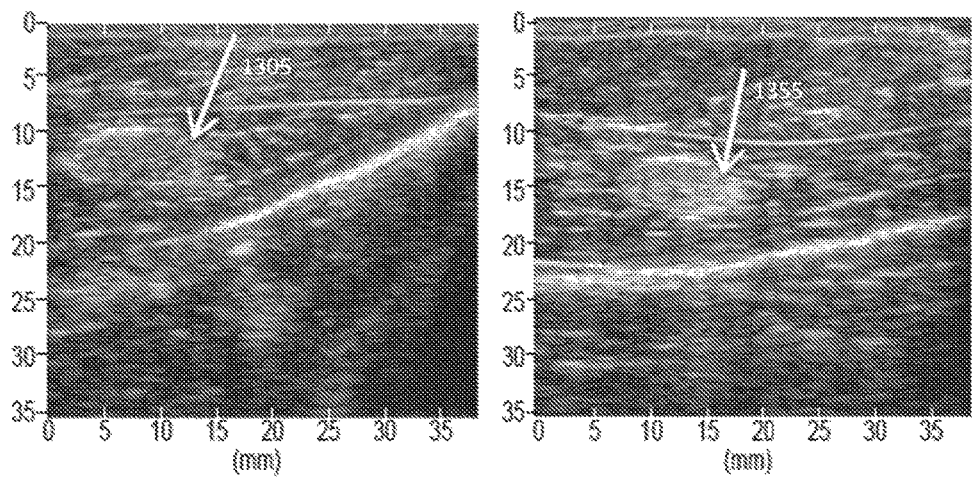
FIG. 13 depicts scan images of a target anatomy taken by one embodiment of the present invention.

FIG. 13 is a scan of a sciatic nerve of a rabbit with a clinical ultrasound array system before and after euthanizing the rabbit to be sure that the nerve could be seen in both cases. FIG. 13 depicts b-mode images (nerve cross-sectional view) for alive (left) and dead (right), and you can see the nerve in each case (arrow 1305, arrow 1355).

Figure 14:
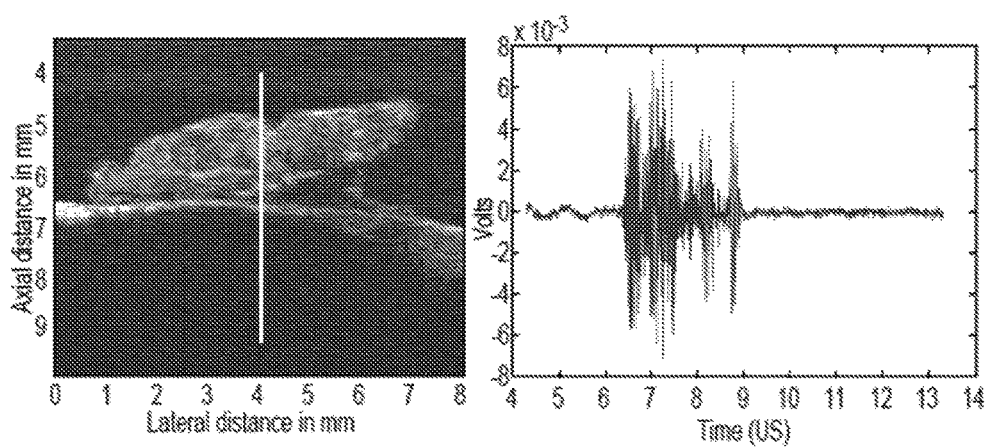
FIG. 14 is a scan and A-line image scan of the target anatomy captured by one embodiment of the present invention.

The nerve was scanned using a high frequency (40 MHz) probe with the bottom of the nerve still attached to the muscle and the nerve centered in the probe's depth of field. The image below (FIG. 14, left) shows a b-mode image of this scan. The image shows (from top to bottom): water, nerve, and muscle. The nerve is separating from the muscle towards the right side of the image, and you can see a gap between the nerve and the muscle. The plot to the right shows the voltage trace from a scan line in the center of the b-mode image, indicated by the white vertical line.

Figure 15:
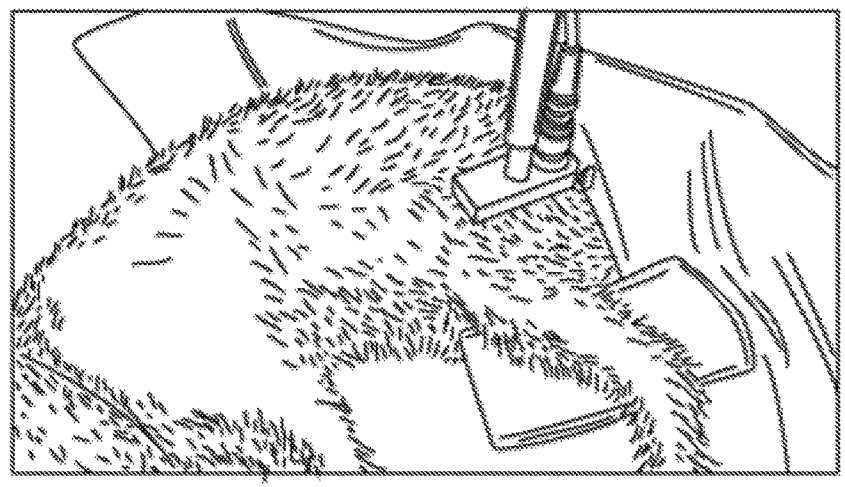
FIG. 15 depicts the configuration of one embodiment of the present invention.

The hind limb sciatic nerve was scanned with a 20 MHz single-element probe though the leg muscle. The muscle was kept intact, and removed the skin to provide a window to see into the muscle. The image shown in FIG. 15 shows the setup.

Figure 16:
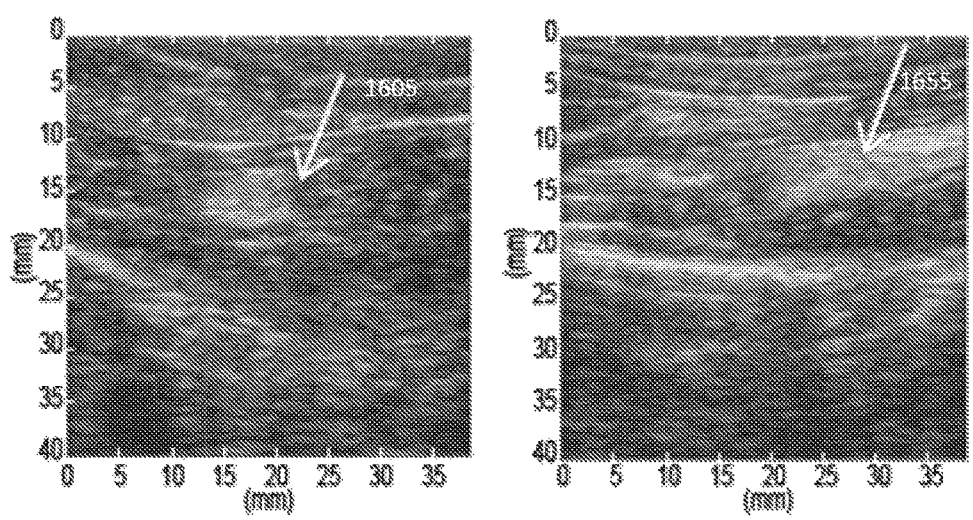
FIG. 16 depicts images of the target anatomy captured by one embodiment of the present invention.
Figure 17:
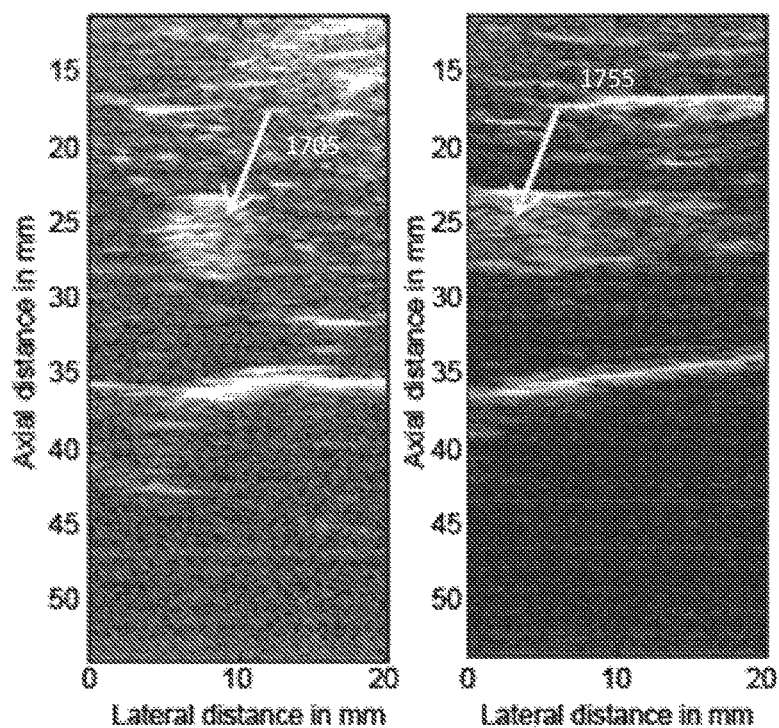
FIG. 17 depicts additional images of the target anatomy captured by one embodiment of the present invention.

A clinical scan was performed before scanning with the 20 MHz probe. An image of the nerve is shown in FIG. 16 (see arrows 1605 and 1655). A comparison between the clinical imaging system figure to the 20 MHz probe figures (shown in FIG. 17, see arrows 1705 and 1755) suggests that both techniques produce similar images.

The cross-section and length-wise (with respect to the long direction of the nerve) scan planes both clearly show the nerve in the background muscle for both the clinical system and the 20 MHz system.

The 20 MHz results are important for at least two reasons:
1. They show that the contrast inside the muscle exists at 20 MHz as demonstrated in the left image in FIG. 17.
2. The depth of penetration for the 20 MHz signal was sufficient to be seen at more than 1 cm of depth. This is the distance away from the surgical probe required for detecting the nerve. Therefore, this suggests that if the signals can be used to detect the nerve, the signal strength and penetration should not be an issue at the chosen ultrasound frequencies.

Figure 18:
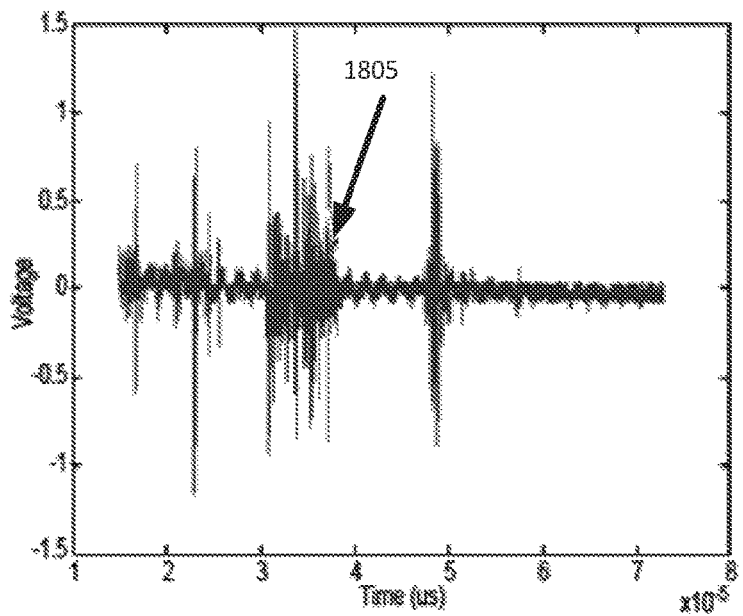
FIG. 18 is a scan of the target anatomy captured by one embodiment of the present invention.

FIG. 18 depicts a single scan lines through the nerve (see arrow 1805). There are characteristic signatures from the nerves that can be used to detect the nerve from a single scan line.

The detection of the nerve (or any other anatomical feature) can be automated and once detected give an audio or visual signal such as "beeping" sound or a flashing light signal (or similar signal) to a physician that they are within a certain distance from the nerve.

It is contemplated that automatic detection of nerve based on single scan lines. The automatic detection would compare the b-mode scan lines captured by the probe with the known scan lines of the target anatomy. The detection system would notify the user of the captured scan lines is identical to, or within a certain predetermined value of, the known scan lines of the target anatomy (e.g. unique signature). The detection system may also be calibrated to determine the proximity of the tip of the probe to the target anatomy and notify the operator when the tip of the probe is within a set distance (e.g. 1 mm). Furthermore, the system will be configured to notify the user the spatial location of the target anatomy and inversely the spatial location of non-target anatomy.

Figure 19:
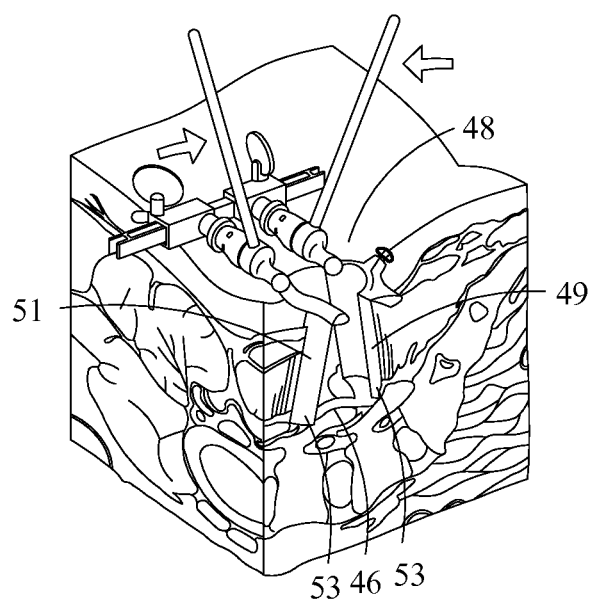
FIG. 19 depicts one embodiment of a retractor system that can be used with embodiments of the present invention.

The present invention is contemplated for being used in connection with minimally invasive surgery (MIS). The device 10 may be used for a variety of MIS procedures, including but not limited to, eXtreme Lateral Lumbar Interbody Fusion (XLIF), Direct Lateral Interbody Fusion (DLIF), Axial Lumbar Interbody Fusion (AxiaLif), Transforaminal Lumbar Interbody Fusion (TLIF), Posterior Lumbar Interbody Fusion (PLIF), Anterior Lumbar Interbody Fusion, Trans-thoracic lumbar interbody fusion, Retropleural Thoracic Fusion, Interbody Fusion utilizing Kambin's Triangle, and Cervical/Thoracic/Lumbar Laminectomies, Foraminotomies and Diskectomies. The device 10 may be used to confirm that the area is clear of other anatomical parts, such as blood vessels, abdominal/pelvic viscera, nerve roots, and spinal cord. As shown in FIG. 19, once at the surgical site 46, the device 10 may be used to illuminate the surgical site 46, to allow the surgeon to introduce instruments (e.g. K-wire) to the surgical site via a conduit formed within the main body 16 of the device 10 or allow a retractor system or dilator system to create direct visualization and a working portal of the surgical site without the device 10.

As described above, there can be a number of applications for which this device 10 may be used, which require the similar steps to access the surgical site. The method of use described below is in connection with performing an XLIF, but it can be appreciated that the device 10 can be used in a similar fashion for performing other MIS procedures as mentioned above.

In operation, the ultrasound imager 24 is used to detect the patient's anatomy as described herein. The surgeon may rely on the image or audio queues generated by the ultrasound imager 24 to detect the presence (or absence) of a nerve thereby allowing the surgery to reposition (or continue advancing) the device 10 through the patient's anatomy towards the surgical site 46. The ultrasound imager 24 may also be used to confirm the image captured by an image capture device (not shown) is accurate by confirming the presence or absence of a targeted anatomical feature (e.g. nerve). The image capture device may consist of a camera or the like disposed within the distal portion 14 of the device 14 so as to capture an image of the region distal to the device 10.

Once the muscles are split and the surgical site 46 is reached, the surgeon can place a k-wire through the conduit to confirm that the surgical site 46 is reached and anchor the device 10 with respect to the surgical site 46. A retractor tool 48 is put into place to give the surgeon a direct surgical working conduit to the surgical site 46. Alternatively, a series of dilators may be sequentially placed over the main body 16 to create the working space. Once this direct access to the spine is achieved, the surgeon is able to perform a standard discectomy (removing the intervertebral disc), corpectomy (removing the vertebral bone) or fusion (uniting two bones together) with surgical tools.

This embodiment of the retractor system 48 includes a first blade 49 and a second blade 51, both of which are semi-circular in shape that form an opening that fits snugly around the outer diameter the main body 16. Once at the surgical site, the retractor blades 49, 51 are configured to separate relative to one another so as to expand the dissection and to enable the device 10 to be removed and allow for direct visualization of the surgical site 46 as shown in FIG. 19. It is contemplated that the distal ends 53 of the first 49 and second 51 blades are adjacent to the distal portion 14 of the main body 12. Any known type retractor system may be used with the device 10.

Figure 20:
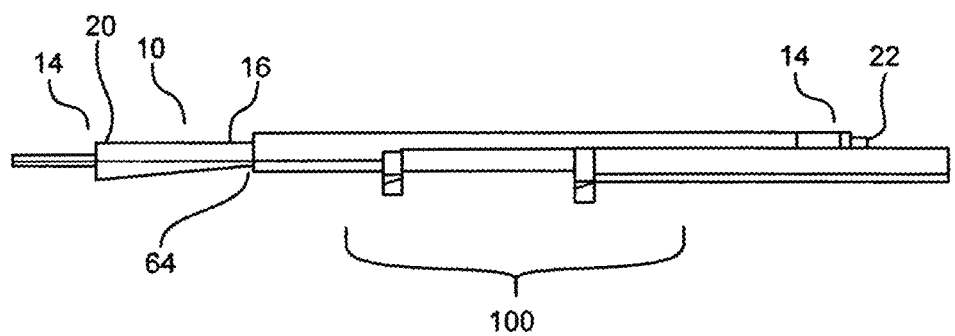
FIG. 20 depicts one embodiment of the dilator system that can be used with embodiments of the present invention.

It is also be appreciated that a series of dilating cannulas (e.g. dilators 100) as shown in FIG. 20, can be slidingly placed around the main body 16 of the device 10 so as to expand the diameter of the dissection made by the distal portion 14 of the device 10. The technique of employing a series of dilating cannulas to create a working space for direct visualization used in other medical procedures to create a working space can also be used in conjunction with the device 10.

After the disc material is removed, the surgeon is able to insert the implant through the same incision from the side. This spacer (cage) will help hold the vertebrae in the proper position to make sure that the disc height (space between adjacent vertebral bodies) is correct and to make sure the spine is properly aligned. This spacer together with the bone graft is designed to set up an optimal environment to allow the spine to fuse at that particular segment. The surgeon will use fluoroscopy to make sure that the spacer is in the right position. The surgeon will then remove the refractor and suture the incisions.

In the alternative, when the tip 22 is disposed adjacent to the psoas muscle, the surgeon may slide a first set of blades of the retractor system over the device and expand the retractor system 48 to create a first working space (also referred to as a superficial dock). This working space will allow the surgeon to visually inspect the psoas muscle and the surrounding region either via naked (eye) inspection or with the optical camera/dissector (Device). Next, the surgeon may continue the procedure by using the device, which is now disposed within the first working space to dissect through the psoas muscle as described herein. Once the tip 22 has reached the surgical site, which is the disc space here, a second set of retractor blades which are smaller than the first set of blades are slid over the device 10 and expanded to create a second working space that is smaller in diameter than the first working space. The surgeon will then continue with the procedure in the manner discussed herein. One benefit of establishing the first working space is that it allows the surgeon to remove the device 10 from the surgical site once the procedure is completed at the first surgical site and reposition and reinsert the distal tip 22 of the device 10 within the first working space that is formed above the psoas muscle at a second location to allow the surgeon to penetrate the psoas muscle to reach a second surgical site to conduct and complete another procedure or a multi-level procedure in which psoas dissection is currently dangerous because o the interposed neurovascular structures (L3-4 and L4-5 disc space or a lumbar corpectomy—removal of two discs and the intervening bone). It is appreciated that the tip 22 is optional and the distal end 21 of the device 10 maybe the portion of the device that is advanced towards the surgical site.

The device 10 may also be used for performing an axial lumbar interbody fusion (ALF). At surgery, the patient is positioned prone with maintenance of lordosis and the legs spread. A catheter is inserted into the rectum will allow air to be injected during the procedure for visualization of the rectum. After the surgeon makes a small incision (15-18 mm) lateral to the tip of the coccyx, the distal tip 22 of the device 10 is inserted through the incision and is passed into the pre-sacral space. The surgeon uses the distal portion 14 of the device 10 to sweep and scan the pre-sacral space to confirm that the space is clear of any offending anatomy (e.g. colon, rectum). The device 10 is gently passed along the anterior cortex of the sacrum and in the midline to an entry point usually close to the S1-2 junction. Once the trajectory is chosen, a sharp beveled pin is then driven into the L5-S1 interspace, either through the conduit 36 or after the retractor system 48 is deployed. The retractor system, 48 or a series of dilators is used to create approximately a 10 mm opening into the sacrum through which a 10 mm channel is drilled into the L5-S1 disc. The device 10 is then withdrawn from the pre-sacral space and the surgeon then performs the remaining steps of the AxiaLIF procedure.

The device 10 may also be used to allow direct access to Kambin's triangle. For this procedure, patients are placed in the prone position typically onto a Jackson Table using a radiolucent frame that allows for restoration of lumbar lordosis. Fluoroscopic imaging is utilized to identify the epiphyseal plate of the upper and lower vertebral body by controlling the cranial-caudal angle of the image intensifier. Additionally, the fluoroscopic image is rotated by 20-35 degrees toward the region, so that the superior articular process can be seen at the middle of the intervertebral disc. At this location, the tip 22 of the device 10 can be inserted percutaneously targeting the area commonly referred to as Kambin's triangle. Kambin's triangle is defined as the area over the dorsolateral disc. The hypotenuse is the exiting nerve root, the base (width) is the superior border of the caudal vertebra and the height is the dura/traversing nerve root.

The device 10 is used to ultrasonically identify various anatomical features such that the exiting root, radicular artery, thecal sac and the disc space. A k-wire can then be place into the disc space via the conduit 36 under ultrasonic detection via the device 10 allowing for docking of the dissector/retractor system 48. Subsequent dilation can then be performed allowing for access in the intervertebral foramen while directly visualizing neurovascular structures using the device and avoiding these structures when identified by the surgeon.

Figure 21:
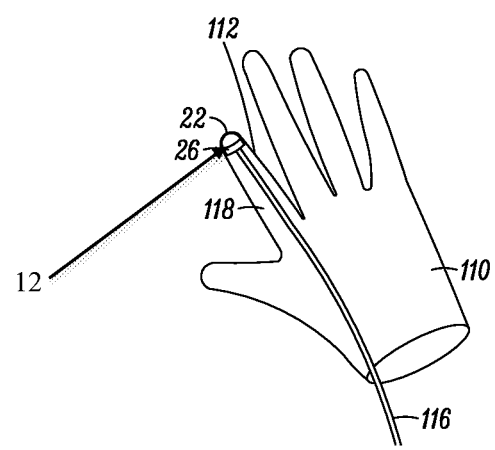
FIG. 21 is one embodiment of the present invention that is incorporated into a glove.

In another embodiment, shown in FIG. 21, an ultrasound imager 24 may be used in conjunction with a glove 110. In this embodiment, the user may rely on tactile feedback provided by touch while still enabling ultrasonic imagining/scanning of a patient's anatomy. More specifically, the glove system (or device) may allow for tactile feedback that facilitates the dissection and separation of tissue namely neurological, vascular and peritoneal structures. In general, tactile feedback allows for dissection of tissue in normal surgical procedures without the unique perspective of direct visualization that is not permissible in minimally invasive/percutaneous techniques.

Figure 22:
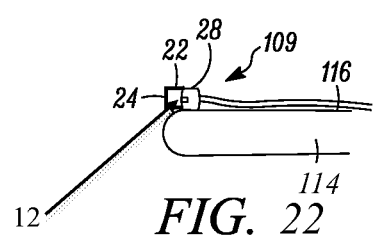
FIG. 22 is a partial side view of the embodiment disclosed in FIG. 21.

The ultrasound imager 24 may include a transducer 26 that is configured to emit sound waves may be disposed at the distal end 20 of the glove 110. In one embodiment, the transducer 26 is located along a distal portion 114 of the index finger 112 of the glove 110. As better shown in FIG. 22, a tip 22 forms part of, or is connected to, the distal portion 114 of the index finger 112 such that the outer surface 24 of the tip 22 does not extend beyond the very most distal part of the index finger 112. Of course, it is appreciated that the tip 22 may extend beyond the distal portion depending on the embodiment.

Connected to the transducer 26 flexible conduit 116 that may carry a cable that connects the transducer 26 to a housing that contains the remaining portion of the ultrasound imager 24. The flexible conduit 116 runs along the length of the index finger 112 and a top portion 118 of the glove 110. However, it can be appreciated that the conduit 116 can run along any length or surface of the glove 110 and is application dependent. The flexible conduit 116 may also provide a channel to carry a k-wire or other instrument that can be slidingly disposed within the flexible conduit 116 (as will be further discussed below). The flexible conduit 116 runs through and is in communication with a unit 109 such that a portion of the flexible conduct 116 provides an opening 120 in the unit 109 at the distal portion 114 of the index finger 114.

Figure 23:
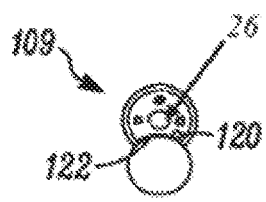
FIG. 23 is a front cross-sectional view of one embodiment of the glove embodiment disclosed in FIG. 21.
Figure 24:
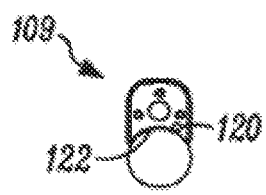
FIG. 24 is a front cross-sectional view of another embodiment of the glove embodiment disclosed in FIG. 21.
Figure 25:
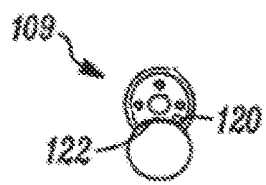
FIG. 25 is a front cross-sectional view of yet another embodiment of the glove embodiment disclosed in FIG. 21.

The unit 109 has a bottom portion 122, as shown in FIG. 23. The bottom portion 122 may have a concave curvature so as to provide a complimentary fit once a user's hand is placed within the glove 109. In addition, a proximal portion 124 of the unit 109 may have a taper so as to cause minimal disruption to a patient's anatomy as the unit 109 is articulated during a procedure. Further, the unit 109 may have an overall semi-circular or cylindrical shape or the like so as to minimize any inadvertent disruption to the patient's anatomy during a procedure and to maintain a small overall profile as shown in FIGS. 24 and 25. For example, the height of the unit 109 may be less than the overall width to as to achieve a low profile. Alternatively, the outer portion of the unit 109 may not extend beyond and become collinear with the width of the index finger 112 to maintain a low profile. The external outer diameter of the unit 109 may range from 0.5 to 20 mm and outside of this range depending on the desired application. The length of the unit 109 can range from 0.5 to 10 mm but also may fall outside of this range depending on the application. It is appreciated that more than one transducer 26 may be positioned along the distal portion of a finger such that they provide side facing scans to generate a multi-directional (e.g. 180°-300°) scan of the patient's anatomy.

It is appreciated that the transducers 26 may be side positioned (e.g. on either side of the index finger 112) so as to provide for multi-directional scanning of the patient's anatomy to detect the nerve or target anatomy. The side positioned transducers are configure to scan the anatomy around in a circumferential direction around the index finger 112 to detect the nerve (or other target anatomy) that was not detected by the transducer positioned at the distal end of the main body 16. The multi-directional scanning enables the system to generate a scan image of the patient's anatomy in multiple directions as the index finger 112 of the glove 110 is advanced through the patient's anatomy. As discussed above, the system that is in communication with the transducers can then detect the nerve even that is not captured by the forward scanning transducer.

The glove embodiment can be used in connection with minimally invasive surgery (MIS). The glove 110 may be used for a variety of MIS procedures, including but not limited to, eXtreme Lateral Lumbar Interbody Fusion (XLIF), Direct Lateral Interbody Fusion (DLIF), Axial Lumbar Interbody Fusion (AxiaLif), Transforaminal Lumbar Interbody Fusion (TLIF), Posterior Lumbar Interbody Fusion (PLIF), Anterior Lumbar Interbody Fusion, Transthoracic lumbar interbody fusion, Retropleural Thoracic Fusion, Interbody Fusion utilizing Kambin's Triangle, and Cervical/Thoracic/Lumbar Laminectomies, Foraminotomies and Diskectomies. The glove 110 may be used to confirm that the area is clear of other anatomical parts, such as blood vessels, abdominal/pelvic viscera, nerve roots, and spinal cord.

As described above, there can be a number of applications for which this glove 110 may be used, which require the similar steps to access the surgical site. The surgeon may rely on the image or audio queues generated by the ultrasound imager 24 to detect the presence (or absence) of a nerve thereby allowing the surgery to reposition (or continue advancing) the glove 110 through the patient's anatomy towards the surgical site 48.

Once the muscles are split and the surgical site 48 is reached, the surgeon can place a k-wire through the conduit to confirm that the surgical site 48 is reached and anchor the glove 110 with respect to the surgical site 48. A retractor tool is put into place to give the surgeon a direct surgical working conduit to the surgical site 48. Alternatively, a series of dilators may be sequentially placed over the k-wire to create the working space. Once this direct access to the spine is achieved, the surgeon is able to perform a standard discectomy (removing the intervertebral disc), corpectomy (removing the vertebral bone) or fusion (uniting two bones together) with surgical tools.

After the disc material is removed, the surgeon is able to insert the implant through the same incision from the side. This spacer (cage) will help hold the vertebrae in the proper position to make sure that the disc height (space between adjacent vertebral bodies) is correct and to make sure the spine is properly aligned. This spacer together with the bone graft is designed to set up an optimal environment to allow the spine to fuse at that particular segment. The surgeon will use fluoroscopy to make sure that the spacer is in the right position. The surgeon will then remove the refractor and suture the incisions.

The glove system may also be used for performing an axial lumbar interbody fusion (ALIF). At surgery, the patient is positioned prone with maintenance of lordosis and the legs spread. A catheter is inserted into the rectum will allow air to be injected during the procedure for visualization of the rectum. After the surgeon makes a small incision (15-18 mm) lateral to the tip of the coccyx, the distal portion of the index finger 112 and distal tip 22 is inserted through the incision and is passed into the pre-sacral space. The surgeon uses the index finger 112 to sweep and inspect the pre-sacral space to confirm that the space is clear of any offending anatomy (e.g. colon, rectum) visually and by way of ultrasonic imaging. The index finger 112 is advanced along the anterior cortex of the sacrum and in the midline to an entry point usually close to the S1-2 junction. Once the trajectory is chosen, a sharp beveled pin is then driven into the L5-S1 interspace, either through a conduit or after the retractor system is deployed. The retractor system or a series of dilators is used to create approximately a 10 mm opening into the sacrum through which a 10 mm channel is drilled into the L5-S1 disc. The index finger 112 is then withdrawn from the pre-sacral space and the surgeon then performs the remaining steps of the AxiaLIF procedure.

The glove system 110 may also be used to allow direct access to Kambin's triangle. For this procedure, patients are placed in the prone position typically onto a Jackson Table using a radiolucent frame that allows for restoration of lumbar lordosis. Fluoroscopic imaging is utilized to identify the epiphyseal plate of the upper and lower vertebral body by controlling the cranial-caudal angle of the image intensifier. Additionally, the fluoroscopic image is rotated by 20-35 degrees toward the region, so that the superior articular process can be seen at the middle of the intervertebral disc. At this location, the index finger 112 can be inserted percutaneously targeting the area commonly referred to as Kambin's triangle. Kambin's triangle is defined as the area over the dorsolateral disc. The hypotenuse is the exiting nerve root, the base (width) is the superior border of the caudal vertebra and the height is the dura/traversing nerve root.

The glove system used to identify various anatomical features such that the exiting root, radicular artery, thecal sac and the disc space. A k-wire can then be place into the disc space via the conduit under ultrasonic visualization allowing for docking of the dissector/retractor system. Subsequent dilation can then be performed allowing for access in the intervertebral foramen while directly visualizing neurovascular structures using the device and avoiding these structures when identified by the surgeon.

In an alternative embodiment, the device 10 may also include infrared technology, which includes an infrared emitting light source and an infrared image capture device. The device 10 would include an infrared radiation detecting elements mounted at the distal portion 14 of the device 10. The infrared array is sensitive at e.g. wavelengths from 2 to 14 micrometers. One embodiment of the infrared aspect of this invention uses a two-dimensional array of microbolometer sensor elements packaged in an integrated vacuum package and co-located with readout electronics on the distal tip of the device 10. It is appreciated that the infrared aspect of this invention may used in conjunction with, or separate from, the other embodiments discussed herein. One such infrared system that could be used with the present invention is disclosed in U.S. Pat. No. 6,652,452, the entirety of which is incorporated herein by reference.

The device 10 may also utilize Optical Coherence Tomography (hereinafter "OCT") technology as a stand alone detection system or in conjunction with the other embodiments disclosed herein. OCT is an optical signal acquisition and processing method that generates images using near infrared light. By way of background, OCT performs high-resolution, cross-sectional tomographic imaging of the internal microstructure in materials and biologic systems by measuring backscattered or back-reflected light. OCT images are typically two- or three-dimensional data sets that represent the optical back-scattering in a cross-sectional plane through the tissue. Image resolutions of approximately 1 to 15 μm may be achieved one to two orders of magnitude higher than conventional ultrasound. Imaging can be performed in situ and in real time.

Figure 26:
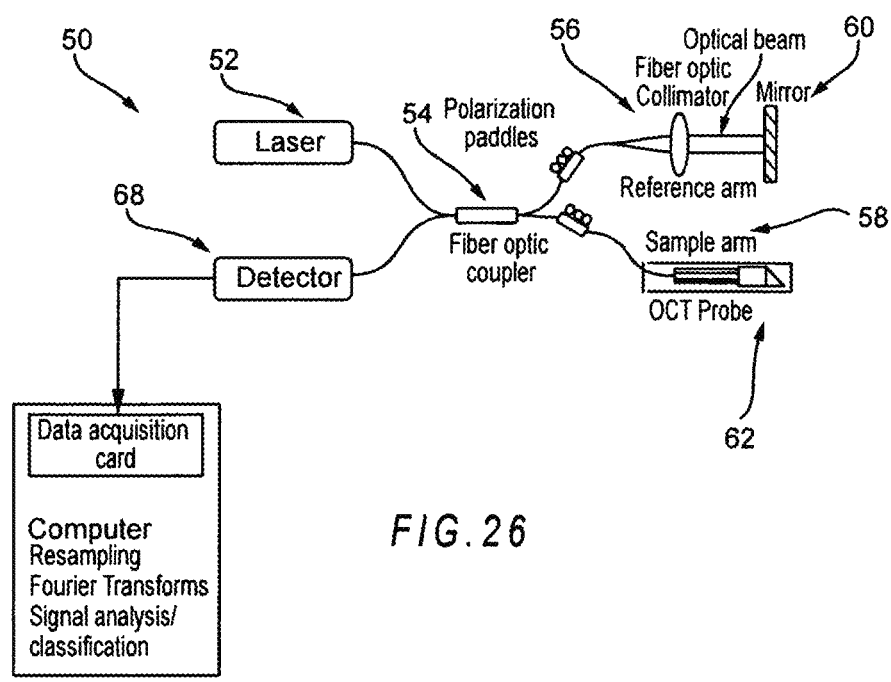
FIG. 26 is diagram of another embodiment of the present invention that utilizes Optical Coherence Tomography.

OCT forms depth resolved images by interferometrically detecting the light backscattered from different scatterers within the sample. In a typical OCT system 50, as shown in FIG. 26, the light from the laser 52 is split by a fiber optic coupler/beam splitter 54 into two arms i.e. the reference arm 56 and the sample arm 58. The light coupled into the reference arm 56 is reflected back from a fixed mirror 60, while in the sample arm 58 the light is projected through an OCT probe 62, which will be discussed in greater detail below.

The OCT probe 62 is focused onto the sample of interest (e.g. tissue or the anatomy of the patient) through a focusing lens (e.g. a GRIN lens). OCT is a point by point imaging technique where the sample is illuminated by focusing the light from the laser 52 onto a small point (spot size determined by the focusing lens) on the sample. Light in the sample arm 58 travels within the tissue and is backscattered by different scatterers within the tissue and combines with the light from the reference arm 56. If the optical path lengths of the reference 56 and sample 58 arms are matched, an interferogram is formed which can be measured by a photo detector or a spectrometer. The frequency content of the interferogram contains information about the depth and strength of the scatterers that the beam had encountered in the sample. The resulting interferogram is processed to form one-dimensional depth information generally known as an A-scan (a single A-scan would be a single column in the image). The optical beam is then scanned over the sample to generate two- or three-dimensional images. The beam can be scanned using galvanometers in bench-top OCT systems or using MEMS scanners in hand-held OCT devices. This data is sent to and processed by the computer or processor 95.

Figure 27:
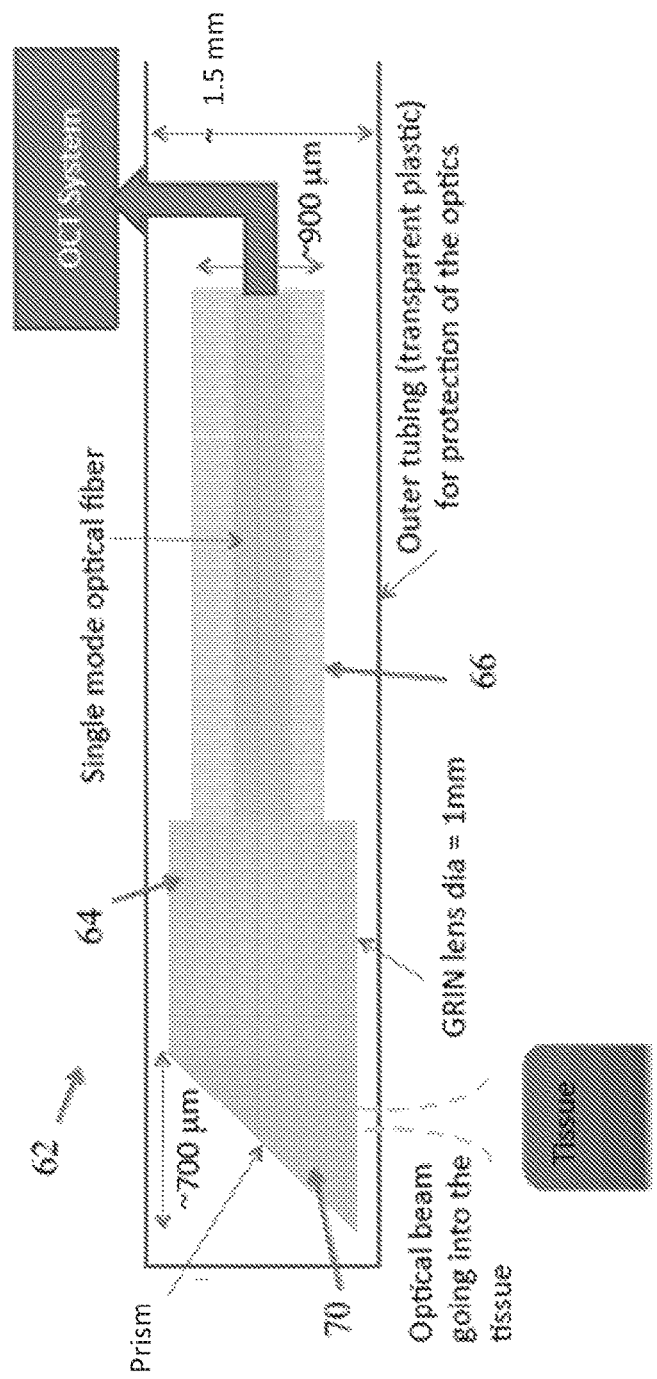
FIG. 27 is one embodiment the probe used with the embodiment disclosed in FIG. 26.

As further disclosed in FIG. 27, the OCT probe 62 may include a GRINS lens 64, the diameter of which in this embodiment is 1 mm, but which can vary depending on the intended application. A single mode optical fiber 66 is included in this embodiment that transfers the light rays between the OCT probe 62 and the remaining portion of the OCT system (e.g. the fiber optic coupler 54 or a detector 68). The single mode optical fiber 66 may have a thickness of approximately 900 μm and a length of approximately 1.5 m. These specifications, of course, are examples only and can vary depending on the application. Attached to the distal end of the GRINS lens 64 may be a prism 70 for deflecting the light depending on the location and orientation of the target. It can be appreciated that the prism 70 may not be necessary in situations where the surface of the target is directly in front of or substantially perpendicular to the longitudinal axis of the light ray (or beam). In this embodiment, the length of the prism is approximately 700 μm, but it is appreciated that the length can vary and is application dependent.

Figure 28:
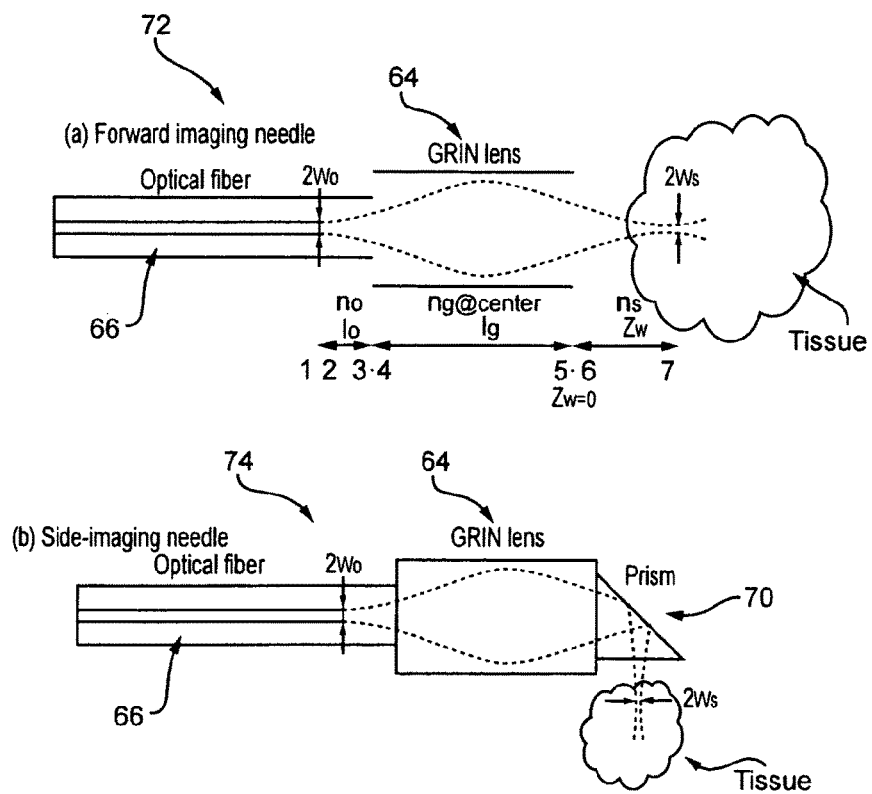
FIG. 28 depicts two embodiments of the probe used with the embodiment disclosed in FIG. 26.

Two different embodiments of the OCT probe 62 are illustrated in FIG. 28. The first embodiment is the forward image probe 72, which does not include a prism 70 such that the light ray (or beam) extends outward towards the front of the probe 72 to reach the target (e.g. tissue). The second embodiment 74 contains a prism 70, which allows this embodiment to image targets that are disposed below or at an angle to the tip of the probe 72. The OCT technology may also be incorporated in to the glove system in a manner discussed above with respect to the ultrasound embodiment 110.

Some of the parameters that may be manipulated to optimize OCT imaging include (a) the A-scan rate (the number of A-scans the system can acquire in a second), (b) the axial and transverse resolution, and (c) the imaging depth. The A-line scan rate would determine how fast an OCT system can operate. For a swept source, the OCT system the rate would depend on the wavelength sweeping rate of the laser while for a spectral domain OCT system it is generally limited by the speed of the line scan camera used in the spectrometer. The tradeoff is that at higher A-scan rate the exposure time has to be reduced which can decrease the SNR of the acquired data. The axial resolution (resolution across the depth) is determined by the bandwidth and wavelength of the laser source. In general, higher the bandwidth the better is the axial resolution. The resolution along the transverse dimensions is determined by the numerical aperture of the lens in the sample arm 58. The higher the numerical aperture, higher the transverse resolution, however, the tradeoff is a reduced depth-of-field. Moreover, with an increase in the center wavelength of the source both the axial and transverse resolutions degrade. Finally, the imaging depth is usually limited by how deeply the light can penetrate through the tissue or sample of interest. Higher wavelengths offer greater imaging depth. These and other parameters may be optimized to detect certain features of a patient's anatomy, such as nerve root.

The OCT probe 62 may be positioned at the distal portion 14 of the device 10. Alternatively, the OCT probe 62 may be positioned at the distal end of a k-wire like structure and disposed through the conduit 36. In either embodiment, the OCT probe 62 is configured to image a portion of the patient's anatomy that is adjacent to (or in front of) the distal portion 14 of the device 10. The surgeon may insert the OCT probe 62 to image the patient's anatomy as needed to reach the surgical site. The OCT system 50 may be configured to visually and/or audibly indicate detection of select preselected portions of a patient's anatomy (e.g. nerve root). As mentioned above, it can be appreciated that the OCT system can be used independently or in combination with other detection technologies described herein.

It is also contemplated that the device 10 can be used in conjunction with a neuromonitoring system to detect certain portions of a patient's anatomy including neural elements that include a nerve, nerve bundle, or nerve root. For the purposes of this discussion, the device 10 and neuromonitoring system will be discussed with respect to detecting a patient's spinal nerve but it is contemplated that the device 10 and neuromonitoring system can be used to detect other nerves (peripheral and central) as well as the spinal cord. One type of neuromonitoring system that can be used in conjunction with the device 10 is disclosed in U.S. Pat. No. 7,920,922, the entirety of which is incorporated by reference herein.

In one embodiment, stimulation electrodes may be placed at the distal end of the device 10, such as forming part of the tip 22, or placed at a distal end of an instrument, such as a K-wire, disposed through the conduit 36, to stimulate any nerves in the region adjacent to the distal portion 14 of the device 10. EMG electrodes can be placed on the skin to detect any nerve depolarization in the manner descried in U.S. Pat. No. 7,920,922. One manner in which the proximity, location, direction, physiology of the nerve is determined is also disclosed in U.S. Pat. No. 7,920,922. It is appreciated that other techniques of detecting nerves using stimulation are known in the art and any of those techniques may be used in conjunction, or integrated, with the device 10 in the manner described above.

The ultrasound imager 24 may be used in conjunction or independent of an image capture device to visualize the patient's anatomy as described herein. One can appreciate that the steps describe herein using the ultrasound imager 24 to detect certain features of a patient's anatomy may by supplemented through use of the an image capture device. Specifically, the surgeon may rely on the image or audio queues generated by the ultrasound imager 24 to detect the presence (or absence) of a nerve thereby allowing the surgery to reposition (or continue advancing) the device 10 through the patient's anatomy towards the surgical site 48. The ultrasound imager 24 may also be used to confirm the image captured by the image capture device is accurate by confirming the presence or absence of a targeted anatomical feature (e.g. nerve).

Likewise, in operation, the OCT system 50 may be used in conjunction or independent of an image capture device and/or the ultrasound imager 24 to scan and identify the patient's anatomy as described herein and to access the surgical site. It is appreciated that steps used to access the surgical site and avoid target anatomy (e.g. nerve) employing the ultrasound imager 24 can also be performed using the OCT system 50. One also appreciates that the steps described herein using ultrasound imager 24 may by supplemented through use of the OCT system 50. For example, the surgeon may rely on the image or audio cues generated by the OCT system 50 to detect the presence (or absence) of a nerve thereby allowing the surgery to reposition (or continue advancing) the device 10 through the patient's anatomy towards the surgical site 48. The OCT system 50 may also be used to confirm the image captured by an image capture device is accurate by confirming the presence or absence of a targeted anatomical feature (e.g. nerve).

While the present invention has been described in terms of preferred examples, and it will be understood that the invention is not limited thereto since modifications may be made to those skilled in the art, particularly in light of the foregoing teachings.

The invention claimed is:

1. A real-time, quantitative method for distinguishing nerve tissue from surrounding tissue during a medical procedure on a mammalian patient, the method comprising:
    ultrasonically scanning, by an array of ultrasound transducers disposed on a device used in said procedure, a region of said patient's anatomy to generate a b-mode image of said region of said patient's anatomy;
    identifying image texture and echogenicity information from a digital representation of anatomical structures in said b-mode image;
    identifying at least one voltage trace associated with an anatomical tissue from at least one scan line from said digital representation of anatomical structures in said b-mode image;
    comparing said at least one identified voltage trace to a predetermined voltage trace representing said nerve tissue;
    determining a presence or an absence of a spectral signature of said nerve tissue in said at least one identified voltage trace based on the comparison;
    determining said anatomical tissue associated with said at least one identified voltage trace to be said nerve tissue if said spectral signature of said nerve tissue is present;
    upon a determination that said anatomical tissue associated with said at least one identified voltage trace is said nerve tissue, generating a 2-dimensional image of said nerve tissue on an output display displaying said b-mode image; and
    generating at least one notification to a user to indicate a proximity of said device to said nerve tissue, wherein said at least one notification includes at least one of a color and an audible alarm indicating that said device is within a predetermined distance of said nerve tissue.

2. The method of claim 1, wherein said at least one notification enables avoidance of said nerve tissue as said device is advanced through said patient's anatomy.

3. The method of claim 1, wherein said device is configured to be rotated about a longitudinal axis of said device for ultrasonically scanning a region of said patient's anatomy extending radially away from said longitudinal axis of said device.

4. The method of claim 1, wherein said device is configured to create a pathway through said patient's anatomy as said device is advanced through said patient's anatomy towards a surgical site, without tearing said patient's anatomy.

5. The method of claim 4, wherein said device is configured to expand said pathway to said surgical site.

6. The method of claim 1, wherein the comparing said at least one identified voltage trace to a predetermined voltage trace representing said nerve tissue comprises determining that a difference between said at least one identified voltage trace and said predetermined voltage trace representing said nerve tissue is less than a determined threshold.

7. The method of claim 1, wherein said predetermined distance is 1 mm.

8. The method of claim 1, wherein said array of ultrasound transducers comprises an array of capacitive micro machined ultrasonic transducers (CMUT).

9. The method of claim 1, wherein said spectral signature is resultant from said ultrasonically scanning.

10. A real-time, quantitative method for distinguishing nerve tissue from surrounding tissue during a medical procedure on a mammalian patient, the method comprising:
    ultrasonically scanning, by a plurality of ultrasound transducers disposed on a device used in said procedure, a region of said patient's anatomy to generate a b-mode image of said region of said patient's anatomy, wherein at least one ultrasound transducer, of said plurality of ultrasound transducers, is angled with respect to a longitudinal axis of said device and configured to scan a region that extends at least partially radially away from said longitudinal axis of said device;
    identifying image texture and echogenicity information from a digital representation of anatomical structures in said b-mode image;
    identifying at least one voltage trace associated with anatomical tissue from at least one scan line from said digital representation of anatomical structures in said b-mode image;
    comparing said at least one identified voltage trace to a predetermined voltage trace representing said nerve tissue;
    determining a presence or an absence of a spectral signature of said nerve tissue in said at least one identified voltage trace based on the comparison;
    determining said anatomical tissue associated with said at least one identified voltage trace to be said nerve tissue if said spectral signature of said nerve tissue is present;
    upon a determination that said anatomical tissue associated with said at least one identified voltage trace is said nerve tissue, generating a 2-dimensional image of said nerve tissue on an output display displaying said b-mode image; and
    generating at least one notification to a user to indicate a proximity of said device to said nerve tissue, wherein said at least one notification includes at least one of a color and an audible alarm indicating that said device is within a predetermined distance of said nerve tissue.

11. The method of claim 10, wherein said device is configured to be rotated about a longitudinal axis of said device for ultrasonically scanning a region of said patient's anatomy extending radially away from said longitudinal axis of said device.

12. The method of claim 10, wherein the comparing said at least one identified voltage trace to a predetermined voltage trace representing said nerve tissue comprises determining that a difference between said at least one identified voltage trace and said predetermined voltage trace representing said nerve tissue is less than a determined threshold.

13. The method of claim 10, wherein said predetermined distance is 1 mm.

14. The method of claim 10, wherein said plurality of ultrasound transducers comprises an array of capacitive micro machined ultrasonic transducers (CMUT).

15. The method of claim 10, wherein said spectral signature is resultant from said ultrasonically scanning.

16. A system for distinguishing nerve tissue from surrounding tissue during a medical procedure on a mammalian patient, the system comprising:
    a scanning device having an array of ultrasound transducers configured to scan a region of said patients anatomy;
    a display device; and
    a computing device in electrical communication with said display device and said scanning device, said computing device configured to:

ultrasonically scan, by said array of ultrasound transducers, said region of said patient's anatomy to generate a b-mode image of said region of said patient's anatomy;

identify image texture and echogenicity information from a digital representation of anatomical structures in said b-mode image;

identify at least one voltage trace associated with an anatomical tissue from at least one scan line from said digital representation of anatomical structures in said b-mode image;

compare said at least one identified voltage trace to a predetermined voltage trace representing said nerve tissue;

determine a presence or an absence of a spectral signature of said nerve tissue in said at least one identified voltage trace based on the comparison;

determine said anatomical tissue associated with said at least one identified voltage trace to be said nerve tissue if said spectral signature of said nerve tissue is present;

upon a determination that said anatomical tissue associated with said at least one identified voltage trace is said nerve tissue, generating a 2-dimensional image of said nerve tissue on said display device displaying said b-mode image; and generate at least one notification to a user to indicate a proximity of said scanning device to said nerve tissue, wherein said at least one notification includes at least one of a color and an audible alarm indicating that said scanning device is within a predetermined distance of said nerve tissue.

17. The system of claim 16, wherein said at least one notification enables avoidance of said nerve tissue as said scanning device is advanced through said patient's anatomy.

18. The system of claim 16, wherein the comparison comprises
a determination that a difference between said at least one identified voltage trace and said predetermined voltage trace representing said nerve tissue is less than a determined threshold.

19. The system of claim 16, wherein said array of ultrasound transducers comprises an array of capacitive micro machined ultrasonic transducers (CMUT).

20. The system of claim 16, wherein said spectral signature is resultant from said scan.

* * * * *